(12) United States Patent
Persoff (10) Patent No.: US 7,338,164 B2
(45) Date of Patent: Mar. 4, 2008

(54) SYSTEMS AND METHODS FOR EYE ABERRATION AND IMAGE SENSOR ORIENTATION

(75) Inventor: Jeffrey Jonathan Persoff, San Jose, CA (US)

(73) Assignee: Visx, Incorporated, Santa Clara, CA (US)

( * ) Notice: Subject to any disclaimer, the term of this patent is extended or adjusted under 35 U.S.C. 154(b) by 610 days.

(21) Appl. No.: 10/839,792

(22) Filed: May 4, 2004

(65) Prior Publication Data

US 2005/0024584 A1 Feb. 3, 2005

Related U.S. Application Data

(60) Provisional application No. 60/491,920, filed on Jul. 31, 2003.

(51) Int. Cl.
*A61B 3/10* (2006.01)
(52) U.S. Cl. .................. 351/205; 351/214; 351/213; 351/216
(58) Field of Classification Search ............. 351/205
See application file for complete search history.

(56) References Cited

U.S. PATENT DOCUMENTS

| | | | |
|---|---|---|---|
| 4,665,913 A | 5/1987 | L'Esperance | |
| 5,646,791 A | 7/1997 | Glocker et al. | |
| 5,683,379 A | 11/1997 | Hohla et al. | |
| 5,713,892 A | 2/1998 | Shimmick | |
| 6,203,539 B1 | 3/2001 | Shimmick | |
| 6,271,914 B1 | 8/2001 | Frey et al. | |
| 6,347,549 B1 | 2/2002 | Ryan et al. | |
| 6,394,999 B1 * | 5/2002 | Williams et al. | 606/5 |
| 6,569,154 B2 * | 5/2003 | Campin et al. | 606/5 |
| 7,040,759 B2 * | 5/2006 | Chernyak et al. | 351/246 |
| 7,196,849 B2 * | 3/2007 | McGuire et al. | 359/630 |
| 2003/0151720 A1 | 8/2003 | Chernyak | |
| 2003/0223037 A1 | 12/2003 | Chernyak | |

* cited by examiner

*Primary Examiner*—Jessica T Stultz
(74) *Attorney, Agent, or Firm*—Townsend & Townsend & Crew LLP; Mark D. Barrish (57) ABSTRACT

Systems and methods orient sensors of an optical system that measures aberrations of an eye. The aberration measurement system may include an optical aberration sensor and an eye image sensor. An asymmetric feature can be imposed in an optical beam path so as to introduce artifacts at the sensors. The optical aberration sensor is often oriented relative to an eye image sensor in response to the asymmetric feature of an optical beam path. In some embodiments, a tool supported by a rail imposes the asymmetric feature on the optical beam path. Aberrations of the eye are measured along the optical beam path with an optical aberration sensor while an eye image sensor forms an image of a tissue structure of the eye positioned along the beam optical path. An aberration correcting shape is identified and ablated in corneal tissue with a laser.

23 Claims, 12 Drawing Sheets

SYSTEMS AND METHODS FOR EYE ABERRATION AND IMAGE SENSOR ORIENTATION

CROSS-REFERENCES TO RELATED APPLICATIONS

This application claim benefit to U.S. Provisional Patent Application No. 60/491,920, filed on Jul. 31, 2003, the disclosure of which is incorporated herein by reference.

BACKGROUND OF THE INVENTION

The present application relates generally to measuring and/or correcting aberrations of an eye. More particularly, the present invention relates to systems and methods for orienting sensors of a wavefront system used to measure aberrations of an eye.

Laser eye surgical procedures often employ some sort of system that measures optical characteristics of a patient's eye. An example of such an eye measurement system is the VISX WaveScan® System, which uses a Hartmann-Shack wavefront sensor. A Hartman-Shack wavefront sensor can quantify aberrations present in an optical system such as an eye. Examples of aberrations include first and second-order aberrations such as prism, sphere and cylinder which are readily corrected with spectacles. Additional aberrations, such as coma and spherical aberration and other third through sixth-order aberrations can also be measured and quantified. A wavefront measurement of an eye creates a high order aberration map that permits assessment of aberrations throughout an optical path of an eye. Contributions of both internal optical tissue surfaces and external optical tissue surfaces to an eye's aberrations are measured. Thereafter, wavefront aberration information can be saved and input into a laser system to compute a custom ablation pattern to correct aberrations present in a patient's eye.

Like many aberration measurement systems, a WaveScan® System also includes a camera ("pupil camera") that takes images of an eye while wavefront measurements are taken with a Hartmann-Shack wavefront sensor. Images of the eye taken with a pupil camera can also be used to track a spatial position of the eye so as to properly align an ablative laser with the eye during a corneal ablation treatment.

Because laser treatment of an eye can be based on an image taken with a pupil camera and a measurement taken with a wavefront sensor, it is important that wavefront data are properly oriented with the image taken with the pupil camera. If the pupil camera and wavefront sensor are not properly oriented when a wavefront measurement is obtained, a subsequent laser assisted corneal ablation may not be properly oriented with the patient's eye.

Manufacture and assembly of systems used to measure an eye can be expensive and time consuming. During assembly of such systems, an incorrect orientation of system components can lead to problems if not detected. Also, detecting an incorrect orientation of a system component can be time consuming. Consequently, systems and methods providing an improved orientation among optical sensors are desirable.

BRIEF SUMMARY OF THE INVENTION

The present invention provides systems and methods for orienting sensors of an optical system that measures aberrations of an eye.

In a first aspect, the present invention comprises a method of locating aberrations of an eye having a tissue structure. An asymmetric feature is imposed in an optical beam path. A first sensor is oriented relative to a second sensor in response to the asymmetric feature of an optical beam path. Aberrations of an eye are measured along the optical beam path with a first sensor, and an image of a tissue structure of an eye positioned along the beam optical path is measured with a second sensor.

In many embodiments, the asymmetric feature induces a first asymmetric artifact at the first sensor and a second asymmetric artifact at the second sensor. The first and second artifact are asymmetric about an axis of an optical sensor. Orienting the first sensor relative to the second sensor comprises identifying an orientational relationship between the first artifact and the second artifact. The aberration correcting shape is identified in response to signals from a first sensor. The aberration correcting shape is aligned with the eye by reference to a tissue structure and ablated with a laser beam. The laser beam is rotationally aligned with the eye about the optical axis of the eye by imaging at least a portion of an iris (or other tissue structure) while the eye is aligned with a laser delivery system.

In specific embodiments the asymmetric feature is imposed by positioning a tool along the optical path such that the tool blocks an asymmetric portion of the optical path. The aberration measurement and pupil image acquisition are performed simultaneously while the tool is clear of the optical beam path. A first orientation of the asymmetric optical beam path is measured with a first sensor and an orientation of the first sensor is determined from a first orientation of an asymmetric optical beam path. A second orientation of an asymmetric optical beam path is measured with a second sensor, and an orientation of a second sensor is determined from a second orientation of an asymmetric optical beam path. A first orientation of an asymmetric optical beam path is compared to a second orientation of an asymmetric optical beam path. A portion of an optical path is blocked with a structure at an oblique angle to an axis of at least one sensor. A first position of a structure is determined with a first optical sensor, and a second position of a structure is determined with a second optical sensor. An orientation of a first sensor is determined from a first position of a structure and an orientation of a second sensor is determined from a second position of a structure.

In another aspect, the present invention comprises a tool for calibrating an aberration measurement system. The aberration measurement system has an optical aberration sensor and an eye image sensor. The optical aberration and eye image sensors are disposed along an optical path with an optical path support structure. The tool comprises a mount configured to engage the optical path support structure so as to position the tool. An optical beam obstruction is affixed to the mount and disposed along the optical path so as to block an asymmetric portion of the path while the mount engages the optical path support structure.

In many embodiments the tool is adapted to block a portion of the path with a structure at an oblique angle to an axis of a sensor. The tool is adapted to be supported by a rail while positioned along the optical path and adapted to be positioned near an aperture formed in a non-transmissive material while the tool is supported by the rail. The eye image sensor comprises a CCD array, and the optical aberration sensor comprises a CCD array.

In specific embodiments, a tool for measuring a first orientation of an optical aberration sensor and a second orientation of an eye image sensor comprises a means for blocking an optical path at an oblique angle. The means for blocking forms an asymmetric optical path. The means for supporting supports the means for blocking while the means for blocking blocks the optical path.

In another aspect the present invention comprises a system for measuring aberrations of an eye having a tissue structure. The system comprises a structure adapted to impose an asymmetric feature in an optical beam path, an optical aberration sensor and an eye image sensor. A relative orientation of the optical aberration sensor and the eye image sensor is identifiable in response to an asymmetric feature of the optical beam path.

In many embodiments, the asymmetric feature induces a first asymmetric artifact at the optical aberration sensor and a second asymmetric artifact at the eye image sensor. The first and second artifacts are asymmetric about an axis of the optical path. The orientation of the optical aberration sensor and the eye image sensor are in response to an orientation between the first artifact and the second artifact. A processor is adapted to identify an aberration correcting shape in response to signals from the optical aberration sensor and to align the aberration correcting shape with the eye by reference to a tissue structure. A laser system is adapted to ablate the aberration correcting shape with a laser beam and rotationally align the laser beam and the eye about an optical axis of the eye. The laser system comprises a camera adapted to image an iris of the eye while the eye is aligned with the laser system. A tissue structure comprises at least a portion of the iris of the eye.

In specific embodiments, a tool is adapted to be positioned along the optical path to block an asymmetric portion of the optical path, so as to impose an asymmetric feature. The optical aberration sensor and the eye image sensor are adapted to measure aberrations and acquire an image of a tissue simultaneously while the tool is clear of the optical beam path. the eye image sensor comprises a CCD array, and the optical aberration sensor comprises a CCD array.

DETAILED DESCRIPTION OF THE INVENTION

The present invention determines an orientation of the Hartmann-Shack camera and an orientation of a pupil camera of a wavefront system. The present invention is particularly useful for enhancing the accuracy and efficacy of laser eye surgical procedures, such as photorefractive keratectomy (PRK), phototherapeutic keratectomy (PTK), laser in situ keratomileusis (LASIK), laser subepithelial keratomileusis (LASEK), and the like. Preferably, the present invention may provide enhanced optical accuracy of refractive procedures by improving a methodology for deriving and orienting a corneal ablation or other refractive treatment program with the patient's eye. The techniques of the invention may be understood with reference to orienting the sensors of the VISX WaveScan Wavefront® System, as described below. It should be appreciated however, that if desired the calibration and orientation methods and devices of the present invention can be used to calibrate and orient sensors of any system measuring aberrations of an eye, such as those manufactured and/or sold by Bausch & Lomb, Wavefront Sciences, Alcon Laboratories, Tracey Technologies, LLC, WaveLight, AG, of Erlangen, Germany, Schwind, GmbH, of Kleinostheim, Germany, Zeiss-Meditec, of Germany, and the like.

While the system and methods of the present invention are described primarily in the context of a laser eye surgery system, it should be understood that the techniques of the present invention may be adapted for use in alternative eye treatment procedures and systems such as radial keratotomy, intraocular lenses, corneal ring implants, collagenous corneal tissue thermal remodeling, and the like.

Figure 1:
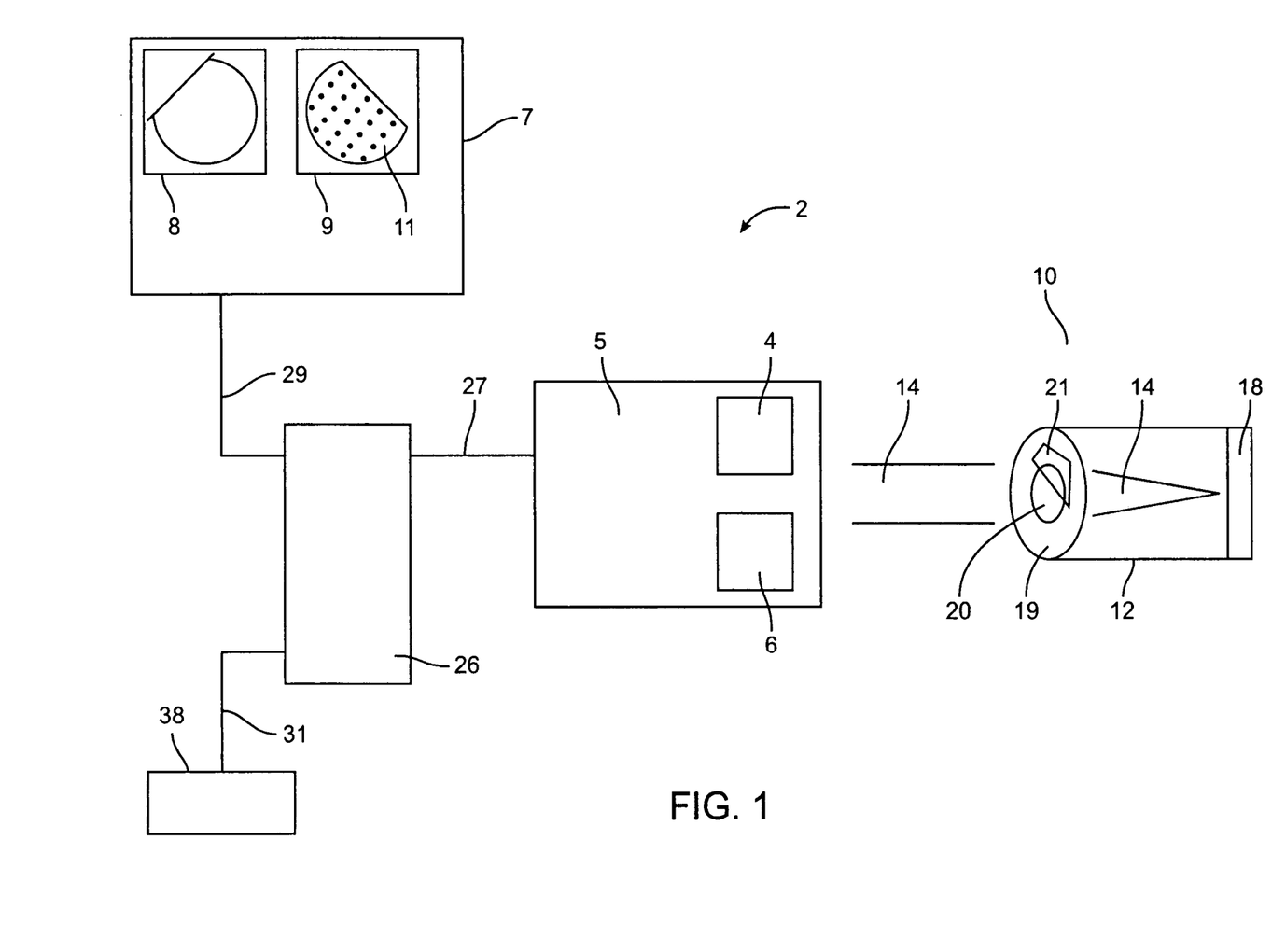
FIG. 1 schematically illustrates a wavefront system having an asymmetric feature imposed on an optical beam path in accordance with an embodiment of the present invention.

FIG. 1 schematically illustrates a wavefront system 2 in accordance with a preferred embodiment of the present invention. Wavefront system 2 includes a calibration system 10. Calibration system 10 includes a reference object, such as a fixture or calibration apparatus 12 that is positioned in an optical path 14 of wavefront system 2. Wavefront system 2 comprises inter alia a Hartmann-Shack camera 4 and a pupil camera 6 for simultaneously obtaining wavefront data and an image of a pupil in an iris of an eye. Wavefront system 2 comprises a head 5 that includes optical components and sensors for taking measurements of the eye. Head 5 is electrically coupled to a computer system 26 with a cable 27. Wavefront system 2 includes a display 7. Display 7 is electrically coupled to a computer system 26 with a cable 29. A pupil camera image 8 and a Hartman-Shack camera image 9 are shown on display 7. A spot pattern 11 formed with a Hartmann-Shack sensor is visible on the Hartmann-Shack camera image 9. In an alternate embodiment, a pupil camera image and an image of a wavefront map of an eye are shown on the display 7. A computer system 26 is electrically coupled to an input device 38 with a cable 31.

Wavefront system 2 generally includes Hartmann-Shack camera 4 that is configured to obtain a wavefront measurement of optical tissues of a patient's eye. Hartmann-Shack camera 4 has a lenslet array (not shown) that records a deviation of rays from a point source on a retina. Wavefront system 2 also includes pupil camera 6, such as a CCD, that is configured to simultaneously record an image of the patient's eye at the time of the wavefront measurement by the Hartmann-Shack camera. A controller, such as a computer system 26 is coupled to cameras 4, 6 for analyzing, calibrating and orienting a wavefront system 2 with images obtained by cameras 4, 6. Computer system 26 may be incorporated into the wavefront system 2, or it may be a separate computer that is coupled to cameras 4, 6.

Light is emitted from a light source (not shown) in wavefront system 2, through an aperture 20 in calibration apparatus 12 and directed and focused onto a target 18. Target 18 is used to reflect a point source of light to Hartmann-Shack camera 4. The light beam is reflected from target 18 back through aperture 20 of calibration apparatus 12 and into the wavefront system 2. A tool 21 is placed near aperture 20 of calibration apparatus 12. Both tool 21 and aperture 20 are placed near an imaging plane of Hartmann-Shack camera 4. Tool 21 imposes an asymmetric feature on an optical beam path. Consequently, a spot pattern that corresponds to an asymmetric feature imposed in the optical beam path appears as an artifact in the image obtained by Hartmann-Shack camera 4. Both tool 21 and aperture 20 are also placed near an imaging plane of a pupil camera 6. Consequently an image that corresponds to the asymmetric feature imposed in an optical beam path appears as an artifact in the image obtained with a pupil camera 6. In one embodiment, aperture 20 is rotationally symmetric and tool 21 imposes an asymmetric feature on optical beam path 14. In other embodiments, however, an aperture 20 may be rotationally asymmetric, so as to impose an asymmetric feature on an optical beam path 14. Pupil camera image 8 and Hartmann-Shack camera image 9 are shown on a display 7. An orientation of Hartmann-Shack camera 4 and pupil camera 6 are determined from displayed images 8 and 9 to determine any incorrect camera orientation.

In one configuration, target 18 has a matte white surface so as to reduce an amount of unwanted light reflections. In another configuration, target 18 comprises Spectralon®, available from Labsphere, of North Sutton, N.H., which reflects optically diffuse light back through a calibration apparatus 12. A calibration fixture is described in U.S. patent application Ser. No. 10/364,973, entitled "Method and Device for Calibrating an Optical Wavefront System," filed on Feb. 11, 2003, the full disclosure of which is incorporated herein by reference.

Figure 2:
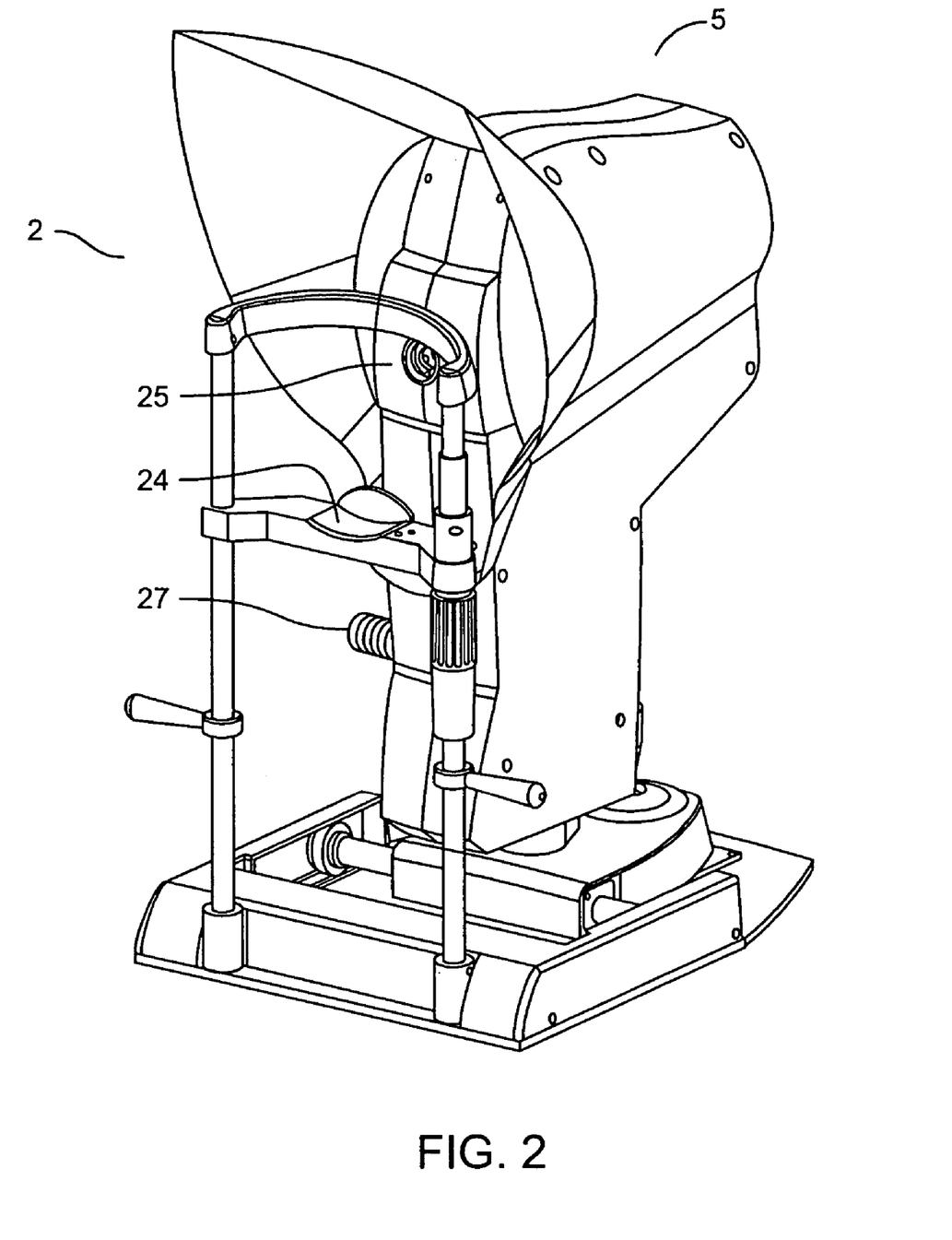
FIG. 2 schematically illustrates a wavefront system in accordance with an embodiment of the present invention.

FIG. 2 schematically illustrates the wavefront system in accordance with an embodiment of the present invention. Wavefront system 2 comprises a head 5 having optical components and sensors for measuring the eye. Wavefront system 2 comprises a chin rest 24 for positioning a patient's head while measurements are taken. Head 5 comprises a threaded member 25 that engages calibration apparatus 12 as described above. A cable 27 electrically couples head 5 with computer system 26. Head 5 includes optical elements (not shown) that form an image of an iris tissue structure from the patient's eye on the pupil camera.

Figure 3:
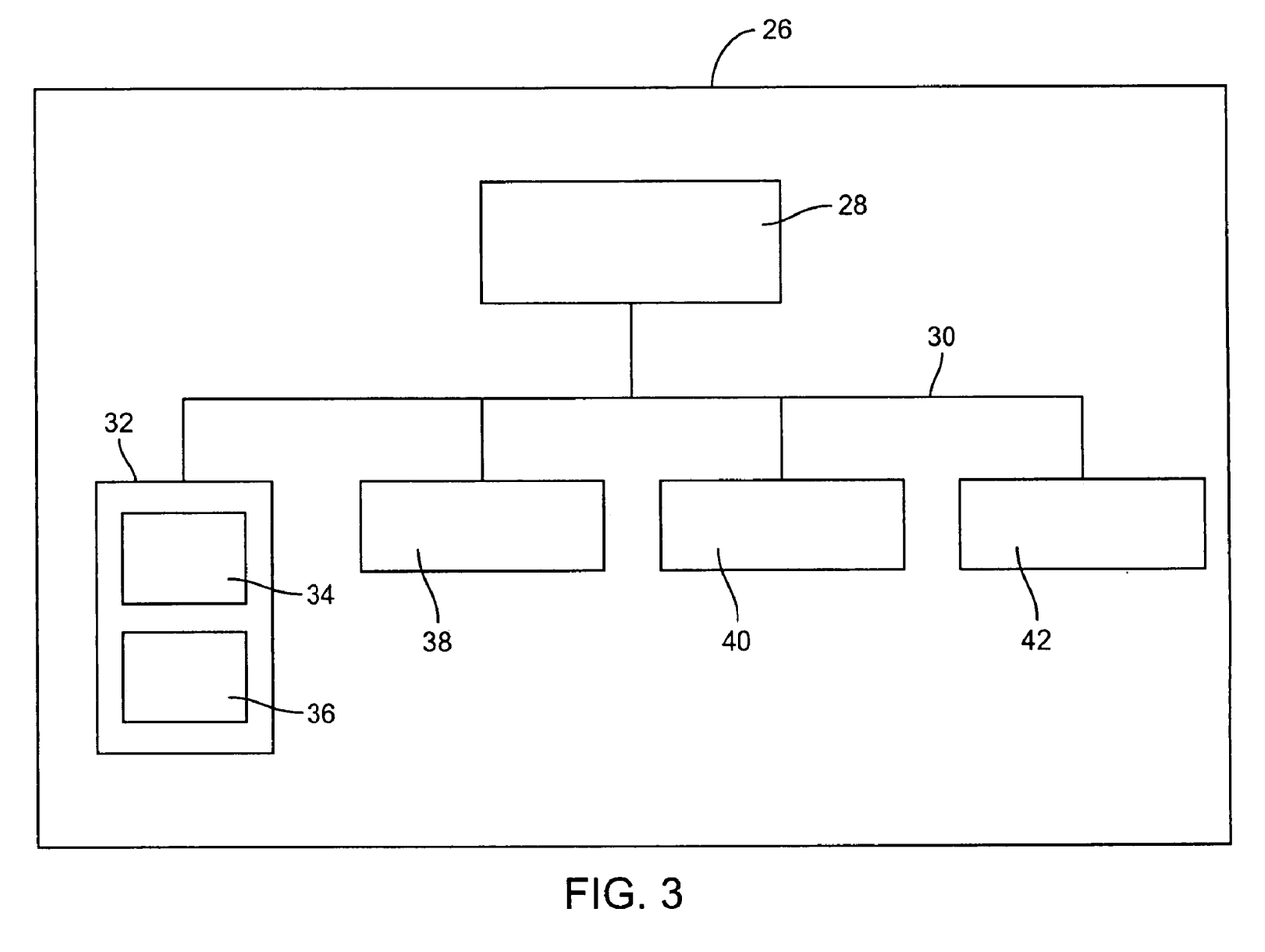
FIG. 3 schematically illustrates a processor of a wavefront system in accordance with an embodiment of the present invention.

FIG. 3 is a simplified block diagram of a computer system 26 that is used to determine an orientation of the Hartmann-Shack camera and the pupil camera using images obtained with cameras 4, 6 in accordance with an embodiment of the present invention. Computer system 26 includes at least one processor 28, which communicates with a number of peripheral devices via a bus subsystem 30. These peripheral devices may include a storage subsystem 32, comprising a memory subsystem 34 and a file storage subsystem 36, user interface input devices 38, user interface output devices 40, and an optional network interface subsystem 42. The input and output devices allow user interaction with computer system 26. A user may be a human user, a device, a process, another computer, and the like.

Network interface subsystem 42 provides an interface to other computer systems and communication networks. Embodiments of network interface subsystem 42 include an Ethernet card, a modem (telephone, satellite, cable, ISDN, etc.), (asynchronous) digital subscriber line (DSL) units, and the like. The computer networks may include the Internet, local area networks (LANs), wide area networks (WAN), wireless networks, intranets, private networks, public networks, switched networks, and the like.

User interface input device 38 may include a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and ways to input information using computer system 26.

User interface output device 40 may include a display subsystem, a printer, a fax machine, or non-visual displays such as audio output devices. The display subsystem may be a cathode ray tube (CRT), a flat-panel device such as a liquid crystal display (LCD), or a projection device. In general, use of the term "output device" is intended to include all possible types of devices and ways to output information from computer system 26.

Storage subsystem 32 may be configured to store the basic software programming and data constructs that provide the functionality of the present invention. For example, according to an embodiment of the present invention, software modules implementing the functionality of the present invention may be stored in storage subsystem 32. These software modules may be executed by processor(s) 28. In a distributed environment, the software modules may be stored on a plurality of computer systems and executed by processors of the plurality of computer systems. Storage subsystem 32 may also provide a repository for storing various databases and data structures that may be used to store information according to the teachings of the present invention. Storage subsystem 32 may comprise memory subsystem 34 and file storage subsystem 36.

Memory subsystem 34 may include a number of memories including a main random access memory (RAM) 44 for storage of instructions and data during program execution and a read only memory (ROM) 46 in which fixed instructions are stored. File storage subsystem 36 provides persistent (non-volatile) storage for program and data files, and may include a hard disk drive, a floppy disk drive along with associated removable media, a Compact Digital-Read Only Memory (CD-ROM) drive, an optical drive, removable media cartridges, CD, DVD, and other like storage media. One or more of the drives may be located at remote locations on other connected computers.

Bus subsystem 30 provides a mechanism for letting the various components and subsystems of computer system 26 communicate with each other as intended. The various subsystems and components of computer system 26 need not be at the same physical location but may be distributed at various locations. Although bus subsystem 30 is shown schematically as a single bus, alternative embodiments of the bus subsystem may utilize multiple buses.

Computer system 26 itself may be of varying types including a personal computer, a portable computer, a workstation, a computer terminal, a network computer, a mainframe, or any other data processing system. Due to the ever-changing nature of computers, the description of computer system 26 depicted in FIGS. 1 and 2 is intended only as a specific example for purposes of illustrating one embodiment of the present invention. Many other configurations of a computer system are possible having more or fewer components than the computer system depicted in FIG. 2.

Figure 4:
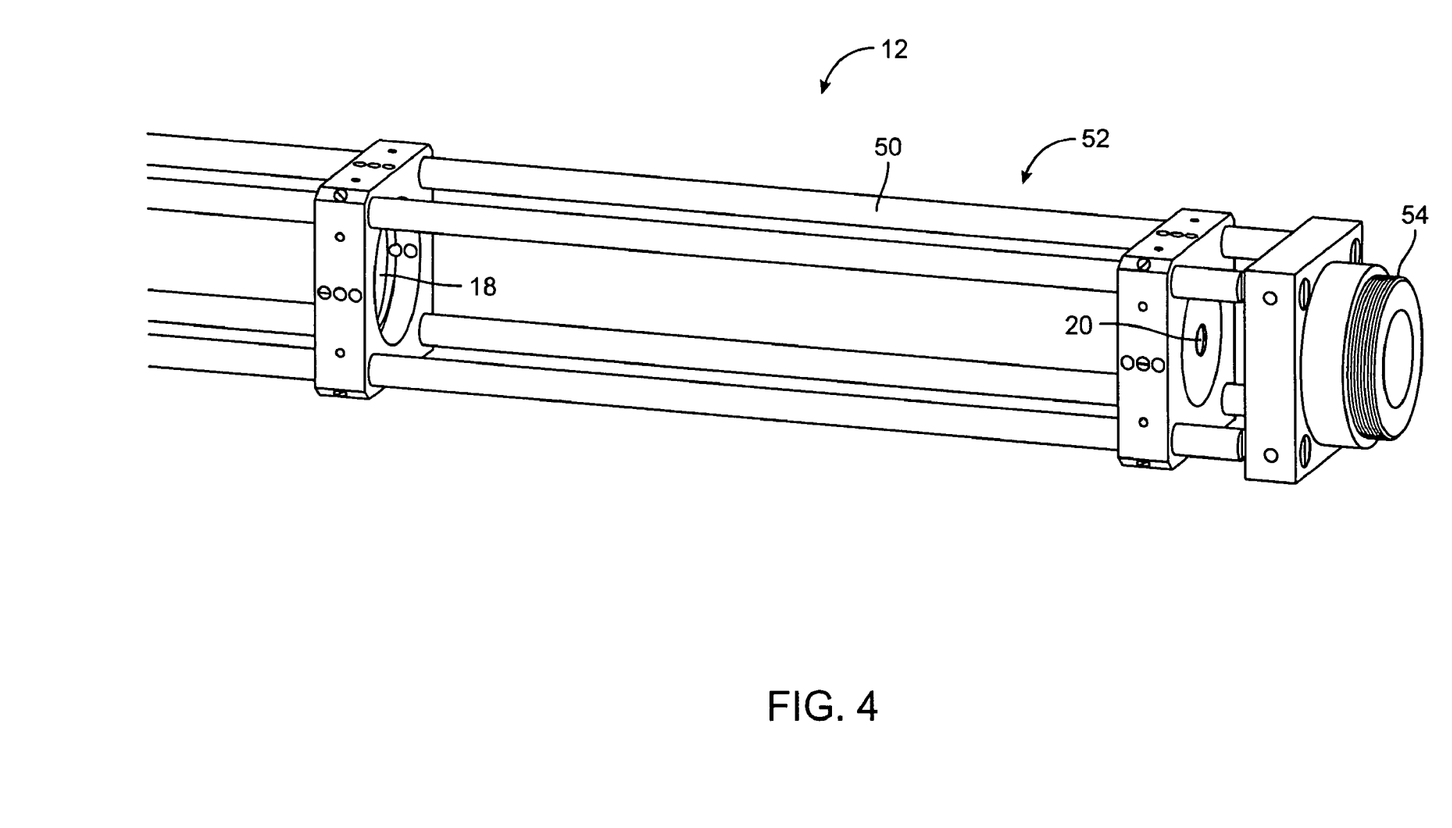
FIG. 4 schematically illustrates a calibration apparatus in accordance with an embodiment of the present invention.

FIG. 4 schematically illustrates the calibration apparatus in accordance with an embodiment of the present invention. Calibration apparatus 12 comprises a threaded member 54 for coupling with wavefront system 2. While calibration apparatus 12 is coupled to wavefront system 2, calibration apparatus 12 acts as an eye and is used to calibrate wavefront system 2. Target 18 is positioned to reflect light back into wavefront system 2 as described above. Aperture 20 is formed in a non-transmissive material as described above. A support structure 52 comprises a rail 50. Support structure 52 supports target 18, aperture 20 formed in non-transmissive material 19 and other components used to calibrate wavefront system 2.

Figure 5:
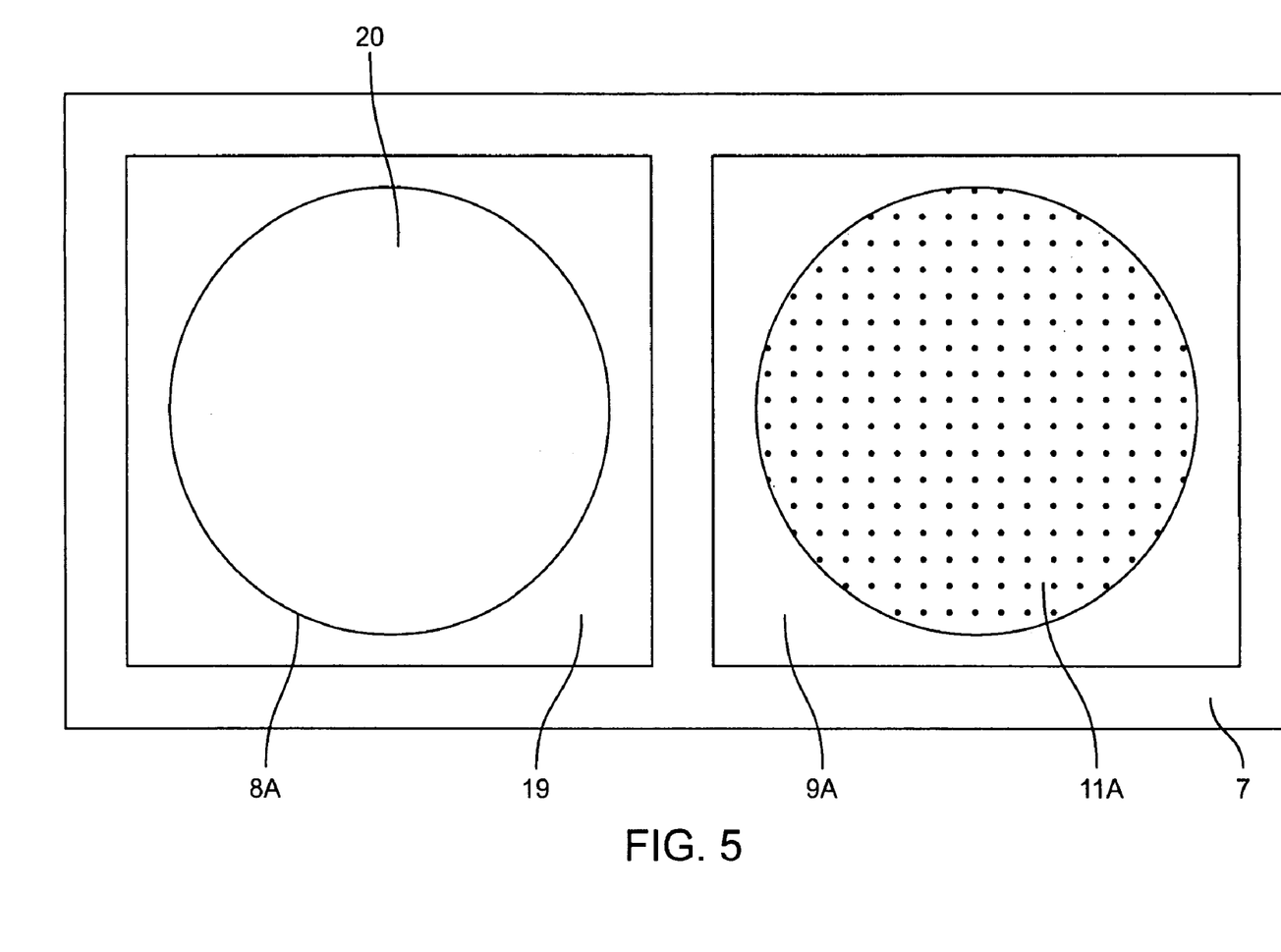
FIG. 5 schematically illustrates an image formed on a CCD array with a Hartmann Shack sensor and an image of an aperture in accordance with an embodiment of the present invention.

FIG. 5 schematically illustrates an image formed on a CCD array with a Hartmann Shack sensor and an image of an aperture in accordance with an embodiment of the present invention. Such an images are obtained with a calibration apparatus having an aperture as described above. Display 7 shows images taken with the Hartman-Shack camera and the pupil camera as described above. A pupil camera image 8A includes an image of a surface of non-transmissive material 19 and an image of aperture 20 formed in non transmissive material 19. Hartmann-Shack camera image 9A has a pattern of spots 11A formed with the Hartmann-Shack sensor.

Figure 6A:
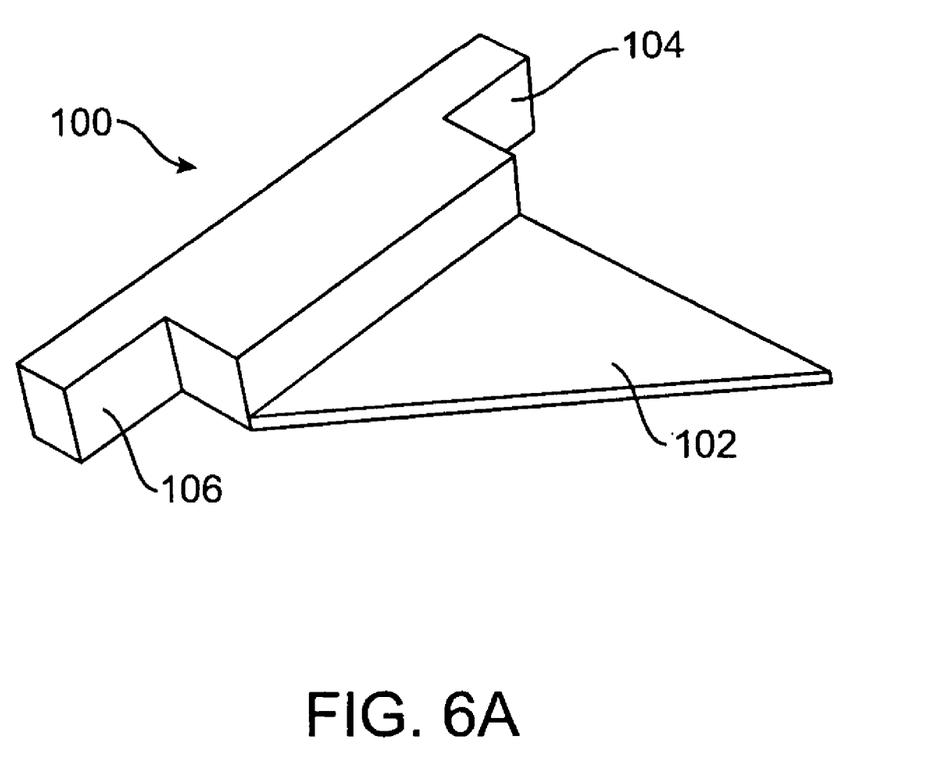
FIG. 6A schematically illustrates a tool for imposing an asymmetric feature in an optical beam path in accordance with an embodiment of the present invention.

FIG. 6A schematically illustrates a tool 100 for imposing an asymmetric feature in an optical beam path in accordance with an embodiment of the invention. Tool 100 comprises a structure 102 for blocking a portion of a beam. Tool 100 comprises surfaces 104 and 106 for supporting tool 100 on rail 50 of the calibration apparatus. Tool 100 is supported on rail 50 while blocking the optical beam path.

Figure 6B:
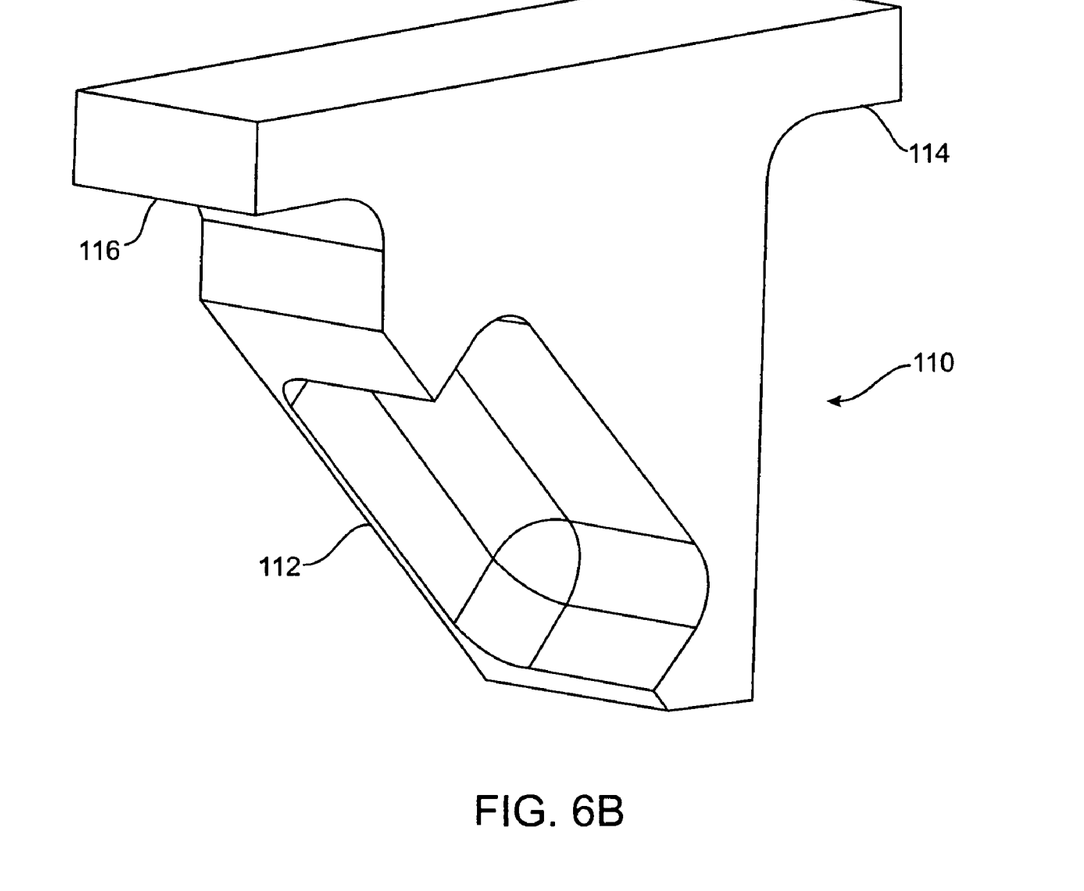
FIG. 6B illustrates a tool for imposing an asymmetric feature in an optical beam path in accordance with a preferred embodiment of the present invention.

FIG. 6B schematically illustrates a tool 110 for imposing an asymmetric feature in an optical beam path in accordance with a preferred embodiment of the present invention. Tool 110 comprises a structure 112 for blocking a portion of the beam. Tool 110 comprises surfaces 114 and 116 for positioning tool 110 on rail 50 of the calibration apparatus. Tool 110 is positioned on rail 50 while blocking the optical beam path.

Figure 7:
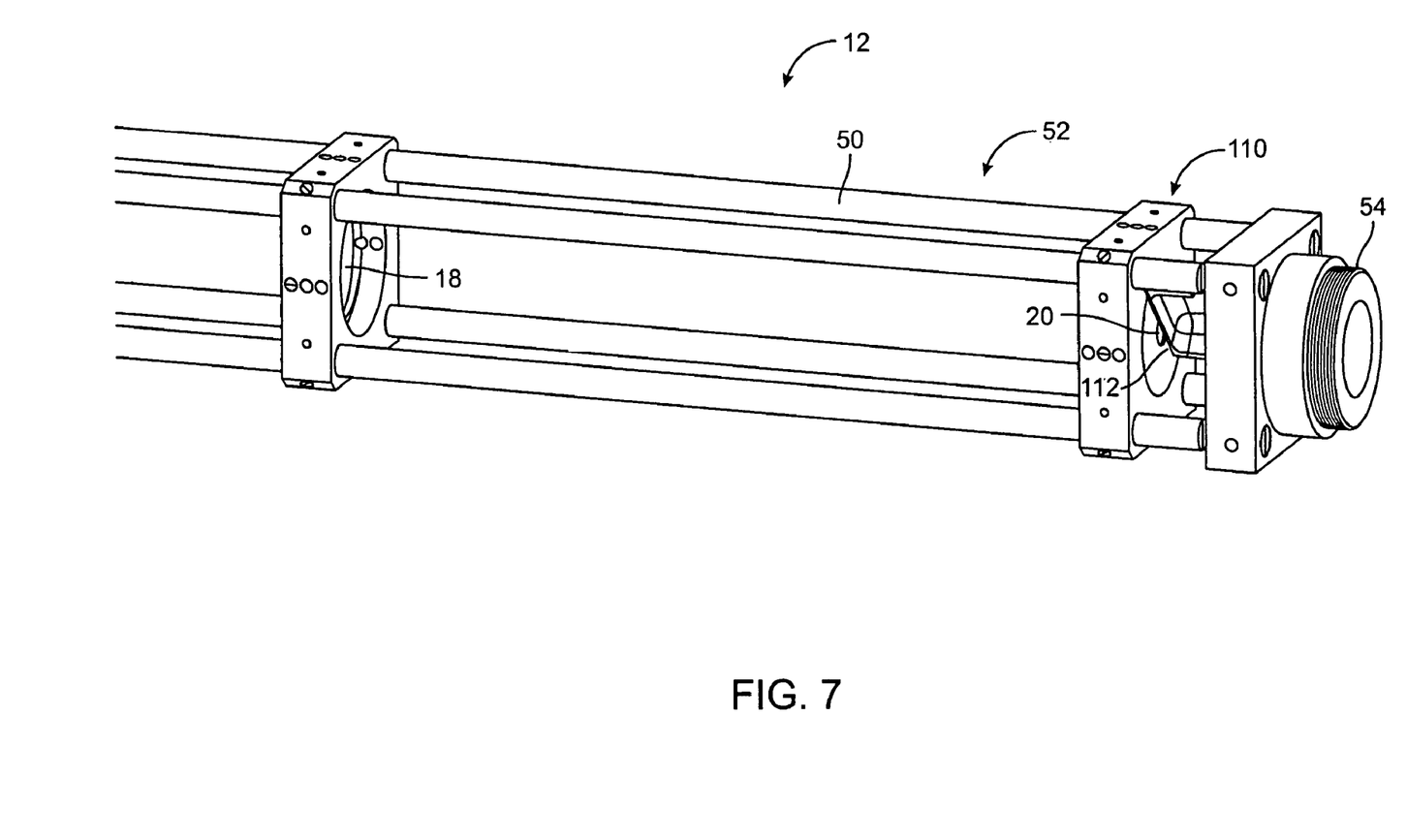
FIG. 7 illustrates a tool imposing an asymmetric feature in an optical beam path while supported on a rail of a calibration apparatus in accordance with a preferred embodiment of the present invention.

FIG. 7 illustrates tool 110 imposing the asymmetric feature in the optical beam path while supported on rail 50 of calibration apparatus 12 in accordance with a preferred embodiment of the present invention. Tool 110 is an obstruction that partially blocks the light beam passing through aperture 20. Tool 110 has structure 112 that imposes an asymmetric feature on the optical beam path with structure 112. Structure 112 is introduced into the optical beam path at an oblique angle to an axis of a sensor. Structure 112 blocks an asymmetric portion of the optical beam path. As illustrated in FIG. 7, structure 112 is introduced into the optical beam path at an angle having a range from about 30 to 50 degrees in relation to a horizontal axis and a vertical axis. In an alternate embodiment an asymmetric feature is imposed on the optical beam path with an asymmetric pupil. For example, an aperture having a shape of a parallelogram having an edge parallel to a horizontal axis and another edge at 45 degrees to a horizontal axis may be formed in the non-transmissive material.

Figure 8:
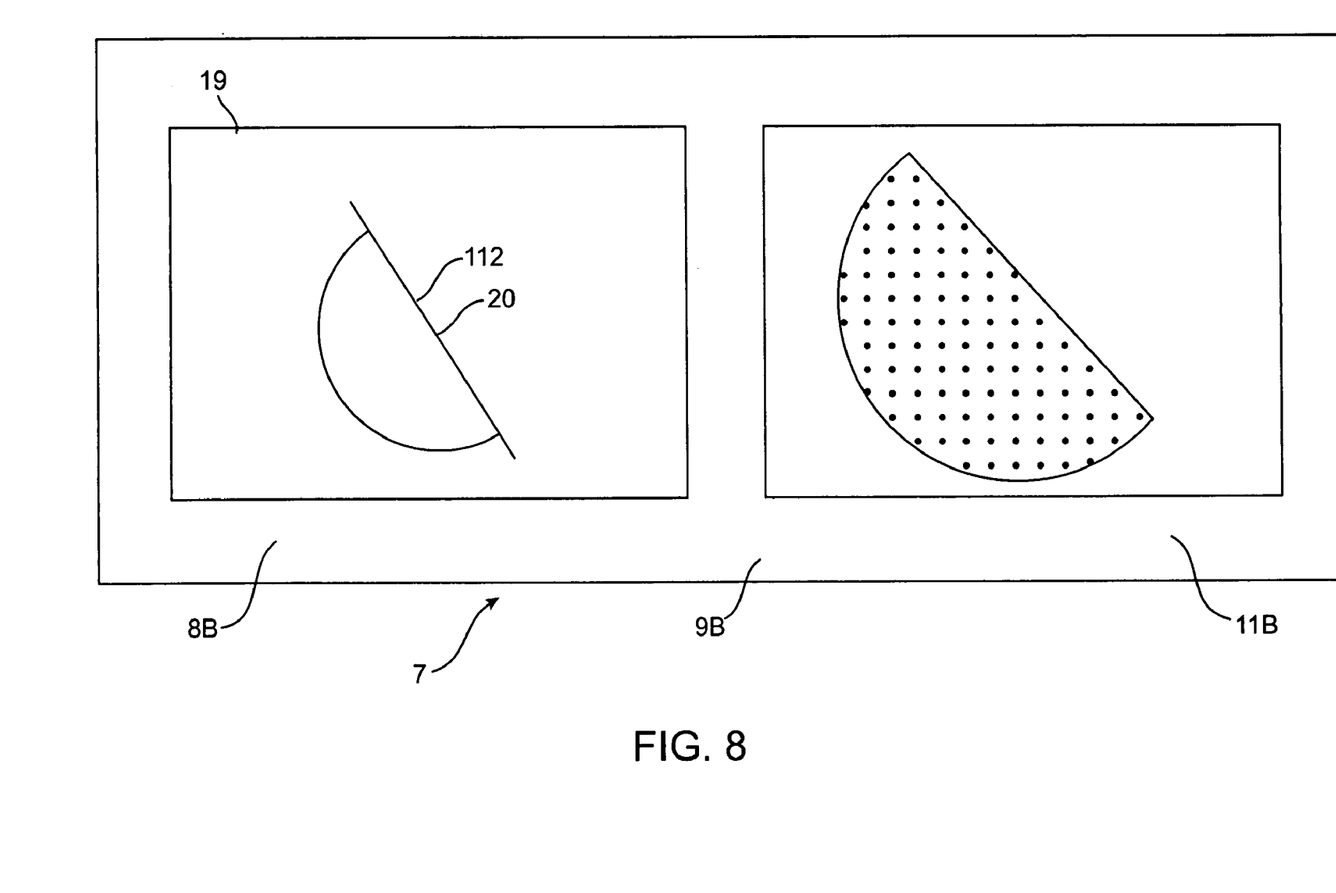
FIG. 8 schematically illustrates an image from a Hartmann Shack camera and an image from a pupil camera while an optical beam is obstructed in accordance with an embodiment of the present invention.

FIG. 8 schematically illustrates an image from the Hartmann Shack camera and an image from the pupil camera while tool 112 obstructs the optical beam path in accordance with an embodiment of the present invention. Such images are obtained with calibration apparatus 12 having aperture 20 as described above. Display 7 shows images taken with the Hartman-Shack camera and the pupil camera as described above. A pupil camera image 8B includes an image of the surface of the non-transmissive material, an image of aperture 20 formed in non transmissive material 19 and an image of structure 112 introduced into the optical beam path so as to cause an artifact on the pupil camera image as described above. A Hartmann-Shack camera image 9B has a pattern of spots 11B formed with the Hartmann-Shack sensor. Spot pattern 9B is asymmetric as shown in FIG. 8. The optical path of the light beam transmitted past aperture 20 and structure 112 is asymmetric.

Figure 8A:
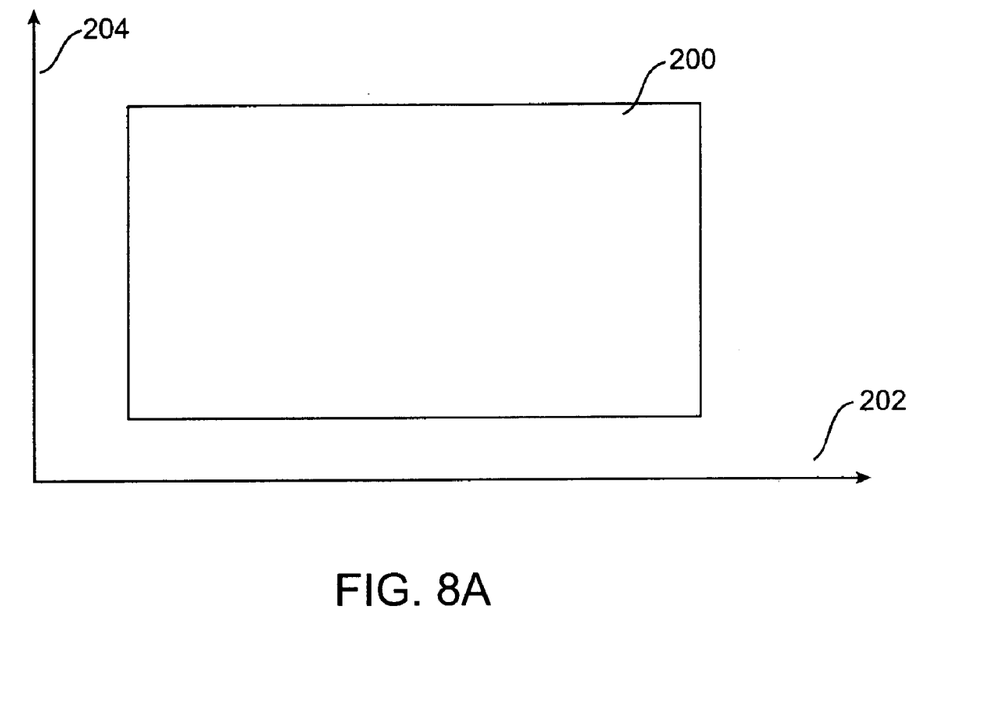
FIG. 8A illustrates axes of a sensor in accordance with an embodiment of the present invention.

FIG. 8A illustrates axes of a sensor in accordance with an embodiment of the present invention. A CCD array 200 comprises a horizontal axis 202 and a vertical axis 204. During assembly and design, an axis of a CCD array can be incorrectly installed. The structure is imposed on the optical beam path as described above, and the optical beam path has an asymmetric feature with respect to an axis of a sensor 200.

Figure 9A:
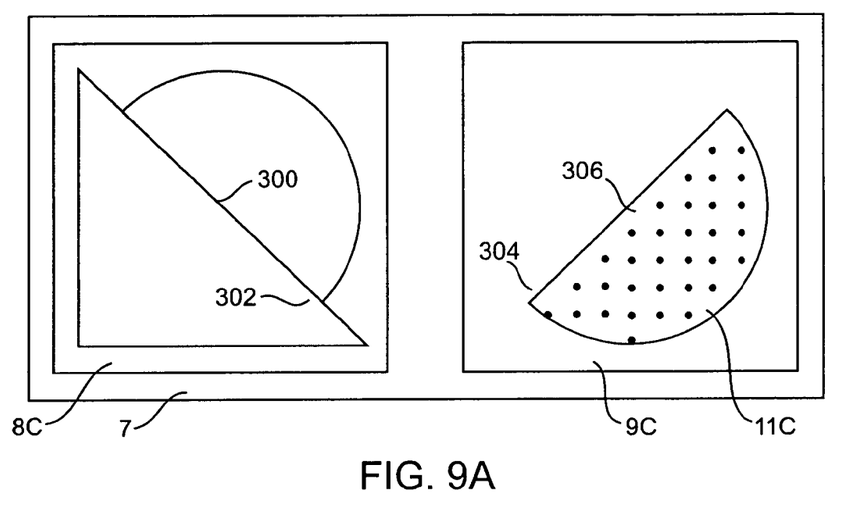
FIGS. 9A and 9B illustrate a method of orienting an optical aberration sensor and an eye image sensor in accordance with a preferred embodiment of the present invention.
Figure 9B:
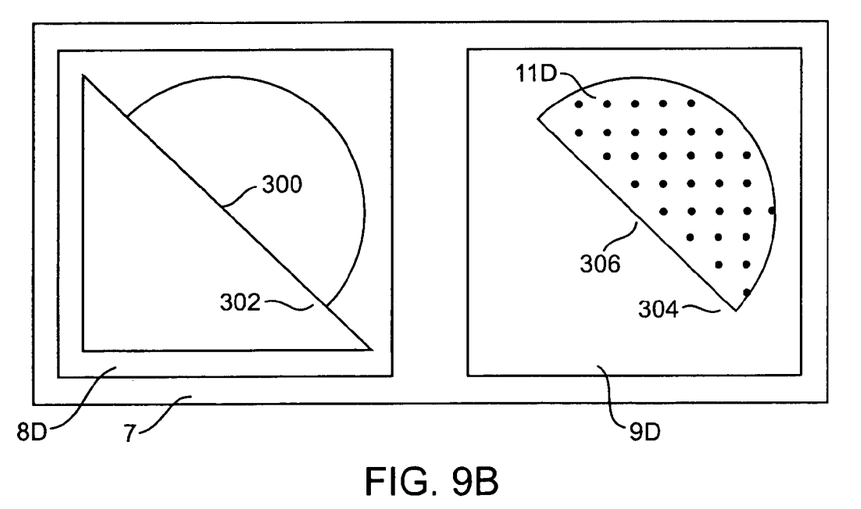

FIGS. 9A and 9B illustrate a method of orienting an optical aberration sensor and an eye image sensor in accordance with a preferred embodiment of the present invention. Referring to FIG. 9A, display 7 shows pupil camera image 8C and a Hartmann-Shack camera image 9C. While the structure is imposed on an optical beam path as described above, an asymmetric artifact 300 appears on pupil camera image 8C and an asymmetric artifact 306 appears on Hartmann-Shack camera image 9C. A position 302 of asymmetric artifact 300 is shown on pupil camera image 8C. A position 304 of asymmetric artifact 306 is shown on Hartmann-Shack camera image 9C. A first position 302 of asymmetric artifact 300 on pupil camera image 8C is compared to a second position 304 of asymmetric artifact 306 on Hartmann-Shack camera image 9C. Alternatively a first position 302 is compared to a reference coordinate system, such as a position of a patient's eye, and a second position 304 is also compared to a reference coordinate system. First position 302 differs from second position 304. The Hartmann-Shack camera as described above is rotated. Alternatively, the pupil camera is rotated. Subsequent to rotation, data are acquired and pupil camera image 8D and Hartmann-Shack camera image 9D are shown on the display as illustrated in FIG. 9B. A first position 302 of an asymmetric artifact 300 on a pupil camera image 8D is compared to a second position 304 of asymmetric artifact 306 on a Hartmann-Shack camera image 9D. First position 302 matches with second position 304, and a pupil camera is oriented with respect to a Hartmann-Shack camera. Alternatively, a first position 304 is compared to a reference coordinate system, and a second position 306 is compared to the coordinate reference system as described above. In an alternate embodiment, images are rotated with a computer program and processor adapted to rotate images as described above. Additional alignment and centering of the pupil camera and the Hartmann-Shack camera can be performed as described in co-pending U.S. patent application Ser. No. 10/365,121, filed Feb. 11, 2003, entitled "Apparatus and Method for Determining Relative Positional and Rotational Offsets Between a First and Second Imaging Device," the full disclosure of which is incorporated herein by reference.

A measurement is taken of the eye with the wavefront system as described above. A treatment shape is identified. Techniques for calculating laser ablation treatments are well known and described in the patent literature. One technique for calculating a shape of tissue to remove is to derive a desired ablation shape from a wavefront elevation map. In such cases, tissue can be removed to adjust an optical surface to a desired shape. A relationship between a depth of material removed and a corresponding change in an optical surface is related to an index of refraction of material removed. For example, the depth of material to be removed can be calculated by dividing the wavefront elevation map by a quantity (n-1) where n is the index of refraction of a cornea. This relation is simply an application of Fermat's principal of least time, known for over 300 years. One embodiment of a technique for such a calculation is also described in U.S. Pat. No. 6,271,914, the full disclosure of which is herein incorporated by reference. Calculations of a laser ablation shape can be made on any processor, including the processor of the wavefront measurement system as described above or a processor of a laser eye surgery system.

Figure 10:
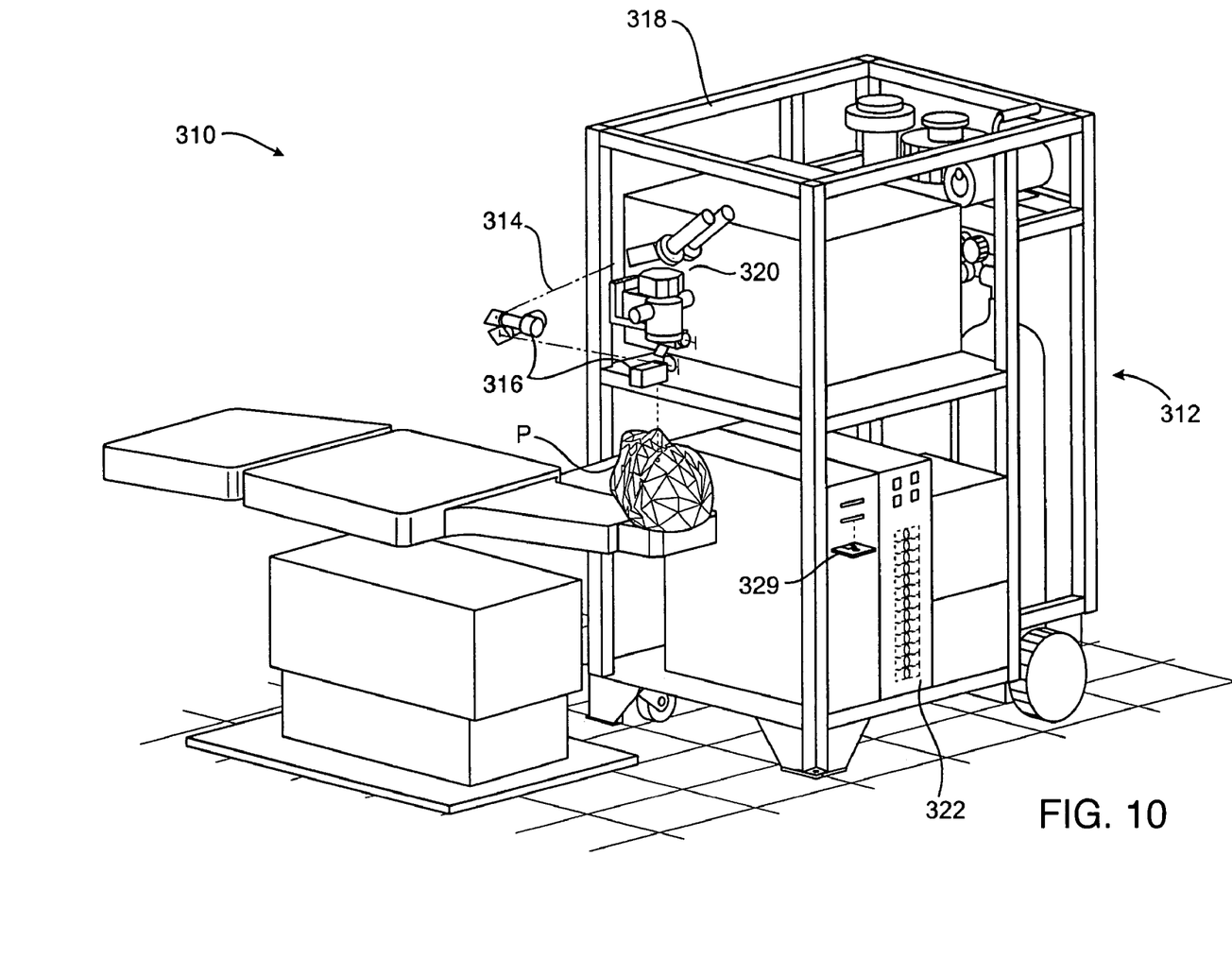
FIG. 10 illustrates a laser eye surgery system in accordance with an embodiment of the present invention.

Referring now to FIG. 10, a laser eye surgery system 310 of the present invention includes a laser 312 that produces a laser beam 314. Laser 312 is optically coupled to laser delivery optics 316, which direct laser beam 314 to an eye of patient P. A delivery optics support structure (not shown here for clarity) extends from a frame 318 supporting laser 312. A microscope 320 is mounted on the delivery optics support structure, the microscope often being used to image a cornea of an eye.

Laser 312 generally comprises an excimer laser, ideally comprising an argon-fluorine laser producing pulses of laser light having a wavelength of approximately 193 nm. Laser 312 will preferably be designed to provide a feedback stabilized fluence at the patient's eye, delivered via delivery optics 316. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. Hence, although an excimer laser is the illustrative source of an ablating beam, other lasers may be used in the present invention.

Laser 312 and delivery optics 316 will generally direct laser beam 314 to the eye of patient P under the direction of a processor 322. Processor 322 will often selectively adjust laser beam 314 to expose portions of the cornea to the pulses of laser energy so as to effect a predetermined sculpting of the cornea and alter the refractive characteristics of the eye. In many embodiments, both laser 312 and the laser delivery optical system 316 will be under computer control of processor 322 to effect the desired laser sculpting process, with the processor effecting (and optionally modifying) the pattern of laser pulses. The pattern of pulses may by summarized in machine readable data of tangible media 329 in the form of a treatment table, and the treatment table may be adjusted according to feedback input into processor 322 from an automated image analysis system (manually input into the processor by a system operator) in response to feedback data provided from an ablation monitoring system feedback system. Such feedback might be provided by integrating the wavefront measurement system described below with the laser treatment system 310, and processor 322 may continue and/or terminate a sculpting treatment in response to the feedback, and may optionally also modify the planned sculpting based at least in part on the feedback.

Laser beam 314 may be adjusted to produce the desired sculpting using a variety of alternative mechanisms. The laser beam 314 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380 filed Nov. 12, 1997; and Ser. No. 09/274,999 filed Mar. 22, 1999, the full disclosures of which are incorporated herein by reference.

Still further alternatives are possible, including scanning of the laser beam over a surface of the eye and controlling the number of pulses and/or dwell time at each location, as described, for example, by U.S. Pat. No. 4,665,913 (the full disclosure of which is incorporated herein by reference); using masks in the optical path of laser beam 314 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 310, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

Processor 322 may comprise (or interface with) a conventional PC system including the standard user interface devices such as a keyboard, a display monitor, and the like. Processor 322 will typically include an input device such as a magnetic or optical disk drive, an internet connection, or the like. Such input devices will often be used to download a computer executable code from a tangible storage media 329 embodying any of the methods of the present invention. Tangible storage media 329 may take the form of a floppy disk, an optical disk, a data tape, a volatile or non-volatile memory, or the like, and the processor 322 will include the memory boards and other standard components of modern computer systems for storing and executing this code. Tangible storage media 329 may optionally embody wavefront sensor data, wavefront gradients, a wavefront elevation map, a treatment map, and/or an ablation table.

In a preferred embodiment, the pupil camera as described above is optically coupled to a laser system 310 to provide torsional alignment and positioning of an eye as described in U.S. patent application Ser. No. 10/300,714, entitled "Methods and Systems for Tracking a Torsional Orientation & Position of an Eye," filed Nov. 19, 2002, the full disclosure of which is incorporated herein by reference. The measurement of aberrations of the eye and the image of an iris tissue structure are taken with the wavefront measurement system as described above. The aberration correcting shape is identified and the treatment calculated as described above. The aberration correcting shape is aligned with an eye by reference to an iris tissue structure. The laser beam and the laser treatment are rotationally aligned with the eye by rotationally aligning the laser beam and the laser beam treatment with the eye about an optical axis of the eye. The pupil camera as described above forms the image of the iris while the eye is aligned with the laser delivery system. The imaged tissue structure of the eye comprises at least a portion of the iris of the eye. The laser beam ablates tissue with a pattern of laser beam pulses so as to ablate the aberration correcting shape in an exposed corneal tissue surface.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method of locating aberrations of an eye, the eye having a tissue structure, the method comprising:
   imposing an asymmetric feature in an optical beam path;
   orienting a first sensor relative to a second sensor in response to the asymmetric feature of the optical beam path;
   measuring aberrations of the eye along the optical beam path with the first sensor; and
   acquiring an image of the tissue structure of the eye along the optical beam path with the second sensor.

2. The method of claim 1, wherein the asymmetric feature induces a first asymmetric artifact at the first sensor, wherein the asymmetric feature induces a second asymmetric artifact at the second sensor, the first and second artifacts being asymmetric about the axis of the optical path, and wherein the orienting step comprises identifying an orientational relationship between the first artifact and the second artifact.

3. The method of claim 1, further comprising identifying an aberration correcting shape in response to signals from the first sensor, and aligning the aberration correcting shape with the eye by reference to the tissue structure.

4. The method of claim 3, further comprising ablating the aberration correcting shape with a laser beam, and rotationally aligning the laser beam and the eye about an optical axis of the eye by imaging an iris of the eye while the eye is aligned with a laser delivery system, the tissue structure comprising at least a portion of the iris of the eye.

5. The method of claim 1, wherein the asymmetric feature is imposed by positioning a tool along the optical path such that the tool blocks an asymmetric portion of the optical path, wherein the aberration measurement and image acquisition are performed simultaneously while the tool is clear of the optical beam path.

6. The method of claim 1, further comprising:
   measuring a first orientation of an asymmetric optical beam path with the first sensor;
   determining an orientation of the first sensor from the first orientation of the asymmetric optical beam path;
   measuring a second orientation of the asymmetric optical beam path with the second sensor; and
   determining the orientation of the second sensor from the second orientation of the asymmetric optical beam path.

7. The method of claim 6 further comprising comparing the first orientation of the asymmetric optical beam path to the second orientation of the asymmetric optical beam path.

8. The method of claim 6 further comprising
   blocking a portion of the optical path with a structure at an oblique angle to an axis of at least one sensor.

9. The method of claim 8 further comprising:
   determining a first position of the structure with the first optical sensor;
   determining a second position of the structure with the second optical sensor; and
   determining the orientation of the first sensor from the first position of the structure and the orientation of the second sensor from the second position of the structure.

10. A tool for calibrating an aberration measurement system, the aberration measurement system having an optical aberration sensor and an eye image sensor, the optical aberration and eye image sensors being disposed along an optical path with an optical path support structure, the tool comprising:
    a mount configured to engage the optical path support structure so as to position the tool; and
    an optical beam obstruction affixed to the mount and disposed along the optical path so as to block an asymmetric portion of the path while the mount engages the optical path support structure.

11. The tool of claim 10 wherein the tool is adapted to block the portion of the path with the structure at an oblique angle to an axis of a sensor.

12. The tool of claim 10 wherein the tool is adapted to be supported by a rail while positioned along the optical path.

13. The tool of claim 12 wherein the tool is adapted to be positioned near an aperture formed in a non-transmissive material while the tool is supported by the rail.

14. The tool of claim 10 wherein the eye image sensor comprises a CCD array.

15. The tool of claim 14 wherein the optical aberration sensor comprises a CCD array.

16. A tool for measuring a first orientation of an optical aberration sensor and an eye image sensor, the tool comprising:
    means for blocking an optical path at an oblique angle to form an asymmetric optical path; and
    means for supporting the means for blocking while the means for blocking blocks the optical path.

17. A system for measuring aberrations of an eye, the eye having a tissue structure, the system comprising:
    a structure adapted to impose an asymmetric feature in an optical beam path;
    an optical aberration sensor; and
    an eye image sensor;
    wherein a relative orientation of the optical aberration sensor and the eye image sensor is identifiable in response to the asymmetric feature of the optical beam path.

18. The system of claim 17, wherein the asymmetric feature induces a first asymmetric artifact at the optical aberration sensor, wherein the asymmetric feature induces a second asymmetric artifact at the eye image sensor, the first and second artifacts being asymmetric about an axis of the optical path, and wherein the orientation of the optical aberration sensor and the eye image sensor are in response to an orientation between the first artifact and the second artifact.

19. The system of claim 17, further comprising a processor adapted to identify an aberration correcting shape in response to signals from the optical aberration sensor and align the aberration correcting shape with the eye by reference to the tissue structure.

20. The system of claim 19, further comprising:
a laser system adapted to ablate the aberration correcting shape with a laser beam and rotationally align the laser beam and the eye about an optical axis of the eye, the laser system comprising a camera adapted to image an iris of the eye while the eye is aligned with the laser system, the tissue structure comprising at least a portion of the iris of the eye.

21. The system of claim 17, further comprising a tool adapted to be positioned along the optical path to block an asymmetric portion of the optical path so as to impose the asymmetric feature, and wherein the optical aberration sensor and the eye image sensor are adapted to measure the aberrations and acquire the image of the tissue simultaneously while the tool is clear of the optical beam path.

22. The system of claim 17 wherein the eye image sensor comprises a CCD array.

23. The system of claim 22 wherein the optical aberration sensor comprises a CCD array.

* * * * *